United States Patent

Filla et al.

[11] Patent Number: 5,905,084
[45] Date of Patent: May 18, 1999

[54] 5-$HT_{1F}$-AGONISTS EFFECTIVE IN TREATING MIGRAINE

[75] Inventors: Sandra A. Filla, Franklin; Brian M. Mathes, Indianapolis; John M. Schaus, Zionsville, all of Ind.

[73] Assignee: Eli Lilly and Company, Indianapolis, Ind.

[21] Appl. No.: 08/970,637

[22] Filed: Nov. 14, 1997

[51] Int. Cl.[6] .......................... A61K 31/44; C07D 47/02
[52] U.S. Cl. ................................ 514/300; 546/113
[58] Field of Search .............. 514/300; 546/113

[56] References Cited

U.S. PATENT DOCUMENTS

| | | |
|---|---|---|
| 5,051,412 | 9/1991 | Macor ................................ 514/300 |
| 5,169,947 | 12/1992 | Macor . |
| 5,521,196 | 5/1996 | Audia et al. . |
| 5,521,197 | 5/1996 | Audia . |
| 5,604,240 | 2/1997 | Chambers et al. . |
| 5,708,008 | 1/1998 | Audia et al. . |

FOREIGN PATENT DOCUMENTS

| | | |
|---|---|---|
| 0379314 | 7/1990 | European Pat. Off. . |
| 2295615 | 6/1996 | United Kingdom . |
| WO 96/29075 | 9/1996 | WIPO . |

*Primary Examiner*—William R. A. Jarvis
*Attorney, Agent, or Firm*—Robert D. Titus

[57] ABSTRACT

This invention provides 5-$HT_{1F}$ agonists of Formula:

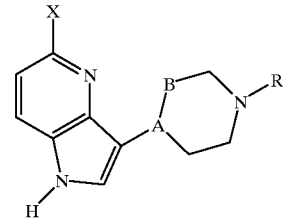

where A-B, X, and R are as defined in the specification. The invention also encompasses pharmaceutical formulations employing the compounds or the invention as well as methods of treating conditions associated with 5-$HT_{1F}$ activation employing these compounds or compositions.

11 Claims, No Drawings

5-HT$_{1F}$-AGONISTS EFFECTIVE IN TREATING MIGRAINE

BACKGROUND OF THE INVENTION

Serotonin (5-HT) exhibits diverse physiological activity mediated by at least seven receptor classes, the most heterogeneous of which appears to be 5-HT$_1$. A human gene which expresses one of these 5-HT$_1$ receptor subtypes, named 5-HT$_{1F}$, was isolated by Kao and coworkers (*Proc. Natl. Acad. Sci. USA*, 90, 408–412 (1993)). This 5-HT$_{1F}$ receptor exhibits a pharmacological profile distinct from any serotonergic receptor yet described.

Moskowitz has proposed that currently unknown triggers for pain stimulate trigeminal ganglia which innervate vasculature within the cephalic tissue, giving rise to release of vasoactive neuropeptides from axons on the vasculature. These released neuropeptides then activate a series of events, a consequence of which is pain. This neurogenic inflammation is blocked by sumatriptan and ergot alkaloids by mechanisms involving 5-HT receptors, believed to be closely related to the 5-HT$_{1D}$ subtype, located on the trigeminovascular fibers (*Neurology*, 43(suppl. 3), S16–S20 (1993)). It has been demonstrated that agonists of the 5-HT$_{1F}$ receptor inhibit peptide extravasation due to stimulation of the trigeminal ganglia (Audia and Nissen, U.S. Pat. No. 5,521,196).

Compounds which exhibit affinity for the 5-HT$_{1F}$ receptor provide a new approach for the treatment of diseases linked to abnormal serotonergic neurotransmission. Furthermore, compounds selective for the 5-HT$_{1F}$ receptor subtype are potentially useful for treating such diseases while causing fewer undesired side effects.

SUMMARY OF THE INVENTION

The present invention provides 5-substituted-3-(piperidin-4-yl)- and 5-substituted-3-(1,2,3,6-tetrahydropyridin-4-yl)pyrrolo[3,2-b]pyridines of Formula I:

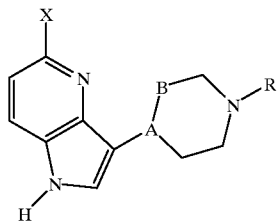

I in which

A-B is —C=CH— or —CH—CH$_2$—;

R is H, C$_1$–C$_6$ alkyl, benzyl, or phenylethyl;

X is halo, hydroxy, C$_1$–C$_4$ alkoxy, —NHR$^1$, —C(O)OR$^2$, or —C(O)NHR$^3$ where:

R$^1$ is C$_1$–C$_4$ alkyl, phenyl(C$_1$–C$_4$ alkylenyl), or heteroaryl (C$_1$–C$_4$ alkylenyl);

R$^2$ is hydrogen or C$_1$–C$_4$ alkyl;

R$^3$ is C$_1$–C$_4$ alkyl, a heterocycle, or phenyl optionally monosubstituted with halo or hydroxy; and pharmaceutically acceptable acid addition salts and solvates thereof, provided that when A-B is —C=CH—, then X is not hydroxy, halogen or C$_1$–C$_4$ alkoxy.

This invention also provides a pharmaceutical formulation which comprises, in association with a pharmaceutically acceptable carrier, diluent or excipient, a compound of Formula I.

A further embodiment of this invention is a method for increasing activation of the 5-HT$_{1F}$ receptor for treating a variety of disorders which have been linked to decreased neurotransmission of serotonin in mammals. Included among these disorders are depression, migraine pain, bulimia, premenstrual syndrome or late luteal phase syndrome, alcoholism, tobacco abuse, panic disorder, anxiety, general pain, chronic pain, post-traumatic syndrome, memory loss, dementia of aging, social phobia, attention deficit hyperactivity disorder, disruptive behavior disorders, impulse control disorders, borderline personality disorder, obsessive compulsive disorder, chronic fatigue syndrome, premature ejaculation, erectile difficulty, anorexia nervosa, disorders of sleep, autism, mutism, allergic rhinitis, trichotillomania, trigeminal neuralgia, dental pain or temperomandibular joint dysfunction pain. The compounds of this invention are also useful as a prophylactic treatment for migraine. Any of these methods employ a compound of Formula II:

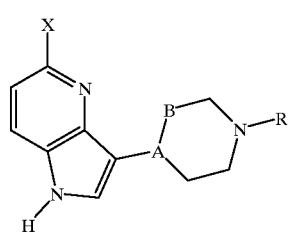

II in which

A-B is —C=CH— or —CH—CH$_2$—;

R is H, C$_1$–C$_6$ alkyl, benzyl, or phenylethyl;

X is halo, hydroxy, C$_1$–C$_4$ alkoxy, —NHR$^1$, —C(O)OR$^2$, or —C(O)NHR$^3$ where:

R$^1$ is C$_1$–C$_4$ alkyl, phenyl(C$_1$–C$_4$ alkylenyl), or heteroaryl (C$_1$–C$_4$ alkylenyl);

R$^2$ is hydrogen or C$_1$–C$_4$ alkyl;

R$^3$ is C$_1$–C$_4$ alkyl, a heterocycle, or phenyl optionally monosubstituted with halo or hydroxy; and pharmaceutically acceptable acid addition salts and solvates thereof.

The use of a compound of Formula II for the activation of the 5-HT$_{1F}$ receptor, for the inhibition of peptide extravasation in general or due to stimulation of the trigeminal ganglia specifically, and for the treatment of any of the disorders described supra, are all embodiments of the present invention.

The present invention also provides processes and synthetic intermediates useful for the preparation of the compounds of the present invention.

DETAILED DESCRIPTION OF THE INVENTION

The general chemical terms used in the formulae above have their usual meanings. For example, the term "alkyl" includes such groups as methyl, ethyl, n-propyl, isopropyl, n-butyl, isobutyl, sec-butyl, tert-butyl, pentyl, 2-pent-yl-, 3-pentyl-, neopentyl, hexyl and the like. The term "alkoxy" includes such groups as methoxy, ethoxy, isopropoxy, sec-butoxy, tert-butoxy, and the like. The term "halo" includes fluoro, chloro, bromo and iodo.

The term "phenyl(C$_1$–C$_4$ alkylenyl)" is taken to mean a branched or linear alkyl chain of 1 to 4 carbon atoms substituted at some point with a phenyl ring and includes such groups as benzyl, phenethyl, phenpropyl and phenbutyl.

The term "heteroaryl($C_1$–$C_4$ alkylenyl)" is taken to mean a branched or linear alkyl chain of 1 to 4 carbon atoms substituted at some point with a heterocycle.

The term "heterocycle" is taken to mean stable aromatic and non-aromatic 5- and 6-membered rings containing carbon and from 1 to 3 heteroatoms selected from the group consisting of nitrogen, oxygen and sulfur, said rings being optionally monobenzofused. These rings include furyl, thienyl, pyridinyl, pyridinyl-N-oxide, pyrrolyl, N-methylpyrrolyl, oxazolyl, isoxazolyl, pyrazolyl, imidazolyl, triazolyl, oxadiazolyl, thiadiazolyl, thiazolyl, pyrimidinyl, pyrazinyl, pyridazinyl, and the like. Benzofused rings include isoquinolinyl, isoquinolinyl-N-oxide, benzoxazolyl, benzthiazolyl, quinolinyl, quinolinyl-N-oxide, benzofuranyl, thionaphthyl, indolyl and the like.

While all of the compounds of this invention are useful as 5-$HT_{1F}$ agonists, certain classes are preferred. The following paragraphs describe such preferred classes.
a) A-B is —C=CH—;
b) A-B is —CH—$CH_2$—;
c) R is $C_1$–$C_6$ alkyl;
d) R is methyl;
e) R is H;
f) X is halo;
g) X is chloro;
h) X is hydroxy;
i) X is $C_1$–$C_4$ alkoxy;
j) X is —$NHR^1$;
k) X is —C(O)$OR^2$;
l) X is C(O)$NHR^3$;
m) $R^1$ is $C_1$–$C_4$ alkyl;
n) $R^1$ is phenyl($C_1$–$C_4$ alkylenyl);
o) $R^1$ is heteroaryl($C_1$–$C_4$ alkylenyl);
p) $R^2$ is hydrogen;
q) $R^2$ is $C_1$–$C_4$ alkyl;
r) $R^3$ is $C_1$–$C_4$ alkyl;
s) $R^3$ is phenyl;
t) $R^3$ is phenyl monosubstituted with halo or hydroxy;
u) $R^3$ is halophenyl;
v) $R^3$ is hydroxyphenyl;
w) $R^3$ is a heterocycle;
x) The compound is a free base;
y) The compound is a salt.

The compounds of the present invention may, depending upon their structure and manner of synthesis and isolation, exist as a pharmaceutically acceptable solvate. These solvates include water, methanol, and ethanol. Solvated forms of the compounds of the present invention represent a further embodiment of the present invention.

The compounds of the present invention where X is hydroxy may exist as a mixture of keto/enol tautomeric forms. The present invention contemplates the keto form, the enol form, and any tautomeric mixtures thereof.

The compounds of this invention are useful in a method for increasing activation of the 5-$HT_{1F}$ receptor for treating a variety of disorders which have been linked to decreased neurotransmission of serotonin in mammals. It is preferred that the mammal to be treated by the administration of compounds of this invention is human.

Since the compounds of this invention are amines, they are basic in nature and accordingly react with any of a number of inorganic and organic acids to form pharmaceutically acceptable acid addition salts. It is preferable to convert the free amines to their pharmaceutically acceptable acid addition salts for ease of handling and administration. Acids commonly employed to form such salts are inorganic acids such as hydrochloric acid, hydrobromic acid, hydroiodic acid, sulfuric acid, phosphoric acid, and the like, and organic acids, such as p-toluene-sulfonic acid, methanesulfonic acid, oxalic acid, p-bromo-phenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid.

The following group is illustrative of compounds of Formula I and II contemplated within the scope of this invention:

5-fluoro-3-(1-hexylpiperidin-4-yl)pyrrolo[3,2-b]pyridine;

5-bromo-3-(1-benzylpiperidin-4-yl)pyrrolo[3,2-b]pyridine;

5-iodo-3-(1-(1-phenyleth-2-yl)piperidin-4-yl)pyrrolo-[3,2-b]pyridine;

5-ethoxy-3-(1-pentylpiperidin-4-yl)pyrrolo[3,2-b]pyridine;

5-propoxy-3-(1-butylpiperidin-4-yl)pyrrolo[3,2-b]pyridine;

5-isopropoxy-3-(1-isobutylpiperidin-4-yl)pyrrolo[3,2-b]pyridine;

5-(N-[methyl]amino)-3-(1-isopropylpiperidin-4-yl)pyrrolo[3,2-b]pyridine;

5-(N-[propyl]amino)-3-(1-ethylpiperidin-4-yl)pyrrolo-[3,2-b]pyridine;

5-(N-[isopropyl]amino)-3-(1-methylpiperidin-4-yl)pyrrolo[3,2-b]pyridine;

5-(N-[butyl]amino)-3-(1-benzylpiperidin-4-yl)pyrrolo-[3,2-b]pyridine;

5-(N-[phenethyl]amino)-3-(1-(1-phenyleth-2-yl)piperidin-4-yl)pyrrolo[3,2-b]pyridine;

5-(N-[phenpropyl]amino)-3-(1-methylpiperidin-4-yl)pyrrolo[3,2-b]pyridine;

5-(N-[phenbutyl]amino)-3-(1-methylpiperidin-4-yl)pyrrolo[3,2-b]pyridine;

5-(N-[3-furylmethyl]amino)-3-(1-methylpiperidin-4-yl)pyrrolo[3,2-b]pyridine;

5-(N-[pyridin-2-ylethyl]amino)-3-(1-methylpiperidin-4-yl) pyrrolo[3,2-b]pyridine;

5-(N-[3-(pyridin-4-yl-N-oxide)prop-1-yl]amino)-3-(1-methylpiperidin-4-yl)pyrrolo[3,2-b]pyridine;

5-(N-[4-(2-pyrrolyl)but-1-yl]amino)-3-(1-methylpiperidin-4-yl)pyrrolo[3,2-b]pyridine;

5-(N-[3-furylmethyl]amino)-3-(1-methylpiperidin-4-yl)pyrrolo[3,2-b]pyridine;

5-(N-[(oxazol-2-yl)methyl]amino)-3-(1-methylpiperidin-4-yl)pyrrolo[3,2-b]pyridine;

5-(N-[(pyrimidin-4-yl)methyl]amino)-3-(1-methylpiperidin-4-yl)pyrrolo[3,2-b]pyridine;

5-(N-[(indol-4-yl)methyl]amino)-3-(1-methylpiperidin-4-yl)pyrrolo[3,2-b]pyridine;

5-(N-[(quinolin-6-yl)methyl]amino)-3-(1-methylpiperidin-4-yl)pyrrolo[3,2-b]pyridine;

N-[3-furyl]-3-(1-methylpiperidin-4-yl)pyrrolo[3,2-b]pyridine-5-carboxamide;

N-[pyridin-2-yl]-3-(1-methylpiperidin-4-yl)pyrrolo[3,2-b]pyridine-5-carboxamide;

N-[pyridin-4-yl-N-oxide]-3-(1-methylpiperidin-4-yl)pyrrolo[3,2-b]pyridine-5-carboxamide;

N-[pyrrol-2-yl]-3-(1-methylpiperidin-4-yl)pyrrolo[3,2-b]pyridine-5-carboxamide;

N-[pyrazol-3-yl]-3-(1-methylpiperidin-4-yl)pyrrolo[3,2-b]pyridine-5-carboxamide;

N-[oxazol-2-yl]-3-(1-methylpiperidin-4-yl)pyrrolo[3,2-b]pyridine-5-carboxamide;

N-[pyrimidin-4-yl]-3-(1-methylpiperidin-4-yl)pyrrolo-[3,2-b]pyridine-5-carboxamide;

N-[indol-4-yl]-3-(1-methylpiperidin-4-yl)pyrrolo[3,2-b]pyridine-5-carboxamide;

N-[quinolin-6-yl]-3-(1-methylpiperidin-4-yl)pyrrolo-[3,2-b]pyridine-5-carboxamide;

5-fluoro-3-(1-hexyl-1,2,3,6-tetrahydropyridin-4-yl)pyrrolo[3,2-b]pyridine;

5-bromo-3-(1-benzyl-1,2,3,6-tetrahydropyridin-4-yl)pyrrolo[3,2-b]pyridine;

5-iodo-3-(1-(1-phenyleth-2-yl)-1,2,3,6-tetrahydropyridin-4-yl)pyrrolo-[3,2-b]pyridine;

5-ethoxy-3-(1-pentyl-1,2,3,6-tetrahydropyridin-4-yl)pyrrolo[3,2-b]pyridine;

5-propoxy-3-(1-butyl-1,2,3,6-tetrahydropyridin-4-yl)pyrrolo[3,2-b]pyridine;

5-isopropoxy-3-(1-isobutyl-1,2,3,6-tetrahydropyridin-4-yl)pyrrolo[3,2-b]pyridine;

5-(N-[methyl]amino)-3-(1-isopropyl-1,2,3,6-tetrahydropyridin-4-yl)pyr-rolo[3,2-b]pyridine;

5-(N-[propyl]amino)-3-(1-ethyl-1,2,3,6-tetrahydropyridin-4-yl)pyrrolo-[3,2-b]pyridine;

5-(N-[isopropyl]amino)-3-(1-methyl-1,2,3,6-tetrahydropyridin-4-yl)pyr-rolo[3,2-b]pyridine;

5-(N-[butyl]amino)-3-(1-benzyl-1,2,3,6-tetrahydropyridin-4-yl)pyrrolo-[3,2-b]pyridine;

5-(N-[phenethyl]amino)-3-(1-(1-phenyleth-2-yl)-1,2,3,6-tetrahydripyridin-4-yl)pyrrolo[3,2-b]pyridine;

5-(N-[phenpropyl]amino)-3-(1-methyl-1,2,3,6-tetrahydro-pyridin-4-yl)pyrrolo[3,2-b]pyridine;

5-(N-[phenbutyl]amino)-3-(1-methyl-1,2,3,6-tetrahydro-pyridin-4-yl)pyrrolo[3,2-b]pyridine;

5-(N-[3-furylmethyl]amino)-3-(1-methyl-1,2,3,6-tetrahydropyridin-4-yl)pyrrolo[3,2-b]pyridine;

5-(N-[pyridin-2-ylethyl]amino)-3-(1-methyl-1,2,3,6-tetrahydropyridin-4-yl)pyrrolo[3,2-b]pyridine;

5-(N-[3-(pyridin-4-yl-N-oxide)prop-1-yl]amino)-3-(1-methyl-1,2,3,6-tetrahydropyridin-4-yl)pyrrolo[3,2-b]pyridine;

5-(N-[4-(2-pyrrolyl)but-1-yl]amino)-3-(1-methyl-1,2,3,6-tetrahydropyridin-4-yl)pyrrolo[3,2-b]pyridine;

5-(N-[3-furylmethyl]amino)-3-(1-methyl-1,2,3,6-tetrahydropyridin-4-yl)pyrrolo[3,2-b]pyridine;

5-(N-[(oxazol-2-yl)methyl]amino)-3-(1-methyl-1,2,3,6-tetrahydropyridin-4-yl)pyrrolo[3,2-b]pyridine;

5-(N-[(pyrimidin-4-yl)methyl]amino)-3-(1-methyl-1,2,3,6-tetrahydropyridin-4-yl)pyrrolo[3,2-b]pyridine;

5-(N-[(indol-4-yl)methyl]amino)-3-(1-methyl-1,2,3,6-tetrahydropyridin-4-yl)pyrrolo[3,2-b]pyridine;

5-(N-[(quinolin-6-yl)methyl]amino)-3-(1-methyl-1,2,3,6-tetrahydropyridin-4-yl)pyrrolo[3,2-b]pyridine;

N-[3-furyl]-3-(1-methyl-1,2,3,6-tetrahydropyridin-4-yl)pyrrolo[3,2-b]pyridine-5-carboxamide;

N-[pyridin-2-yl]-3-(1-methyl-1,2,3,6-tetrahydropyridin-4-yl)pyrrolo[3,2-b]pyridine-5-carboxamide;

N-[pyridin-4-yl-N-oxide]-3-(1-methyl-1,2,3,6-tetrahydropyridin-4-yl)pyrrolo[3,2-b]pyridine-5-carboxamide;

N-[pyrrol-2-yl]-3-(1-methyl-1,2,3,6-tetrahydropyridin-4-yl)pyrrolo[3,2-b]pyridine-5-carboxamide;

N-[pyrazol-3-yl]-3-(1-methyl-1,2,3,6-tetrahydropyridin-4-yl)pyrrolo[3,2-b]pyridine-5-carboxamide;

N-[oxazol-2-yl]-3-(1-methyl-1,2,3,6-tetrahydropyridin-4-yl)pyrrolo[3,2-b]pyridine-5-carboxamide;

N-[pyrimidin-4-yl]-3-(1-methyl-1,2,3,6-tetrahydropyridin-4-yl)pyrrolo-[3,2-b]pyridine-5-carboxamide;

N-[indol-4-yl]-3-(1-methyl-1,2,3,6-tetrahydropyridin-4-yl)pyrrolo[3,2-b]pyridine-5-carboxamide;

N-[quinolin-6-yl]-3-(1-methyl-1,2,3,6-tetrahydropyridin-4-yl)pyrrolo-[3,2-b]pyridine-5-carboxamide;

The compounds of the present invention are prepared by the procedure described in Synthetic Scheme I where X' is halo or $C_1$–$C_4$ alkoxy; and R is as previously defined.

Synthetic Scheme I

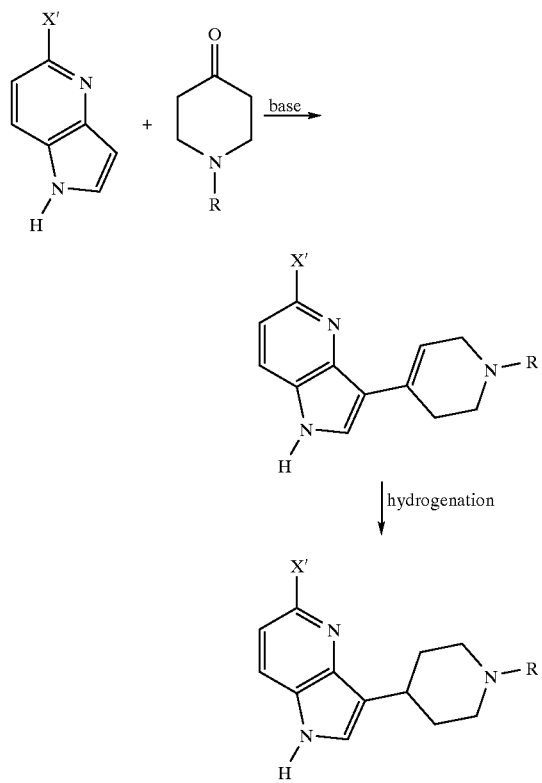

A 5-substituted-pyrrolo[3,2-b]pyridine is condensed with a 4-piperidone in a lower alkanol, typically methanol or ethanol, in the presence of a suitable base. Suitable bases include potassium or sodium hydroxide, and sodium alkoxides such as sodium methoxide. The reaction is performed at reflux to give the corresponding 5-substituted-3-(1,2,3,6-tetrahydropyridin-4-yl)pyrrolo [3,2-b]pyridines of the present invention. Product may be isolated by filtration or extractive workup, and may be purified by recrystallizaton or chromatography if necessary or desired.

The 5-substituted-3-(1,2,3,6-tetrahydropyridin-4-yl) pyrrolo[3,2-b]pyridines of the present invention, while useful 5-HT$_{1F}$ agonists in their own-right, may be hydrogenated to provide the 5-substituted-3-(piperidin-4-yl)pyrrolo[3,2-b] pyridines of the present invention. Typically the conversion is accomplished under standard hydrogenation conditions, for example, hydrogenating a solution of the substrate in a lower alkanol, typically methanol or ethanol, or a mixture of the lower alkanol and tetrahydrofuran, in the presence of a precious metal catalyst, typically either platinum or palladium on carbon.

Compounds of the invention where X is $C_1$–$C_4$ alkoxy are also useful intermediates for the preparation of other compounds of the invention as illustrated in Synthetic Scheme II where $R^2$, is $C_1$–$C_4$ alkyl, and A-B, R, and $R^3$ are as previously defined.

sulfonic anhydride in a suitable solvent, typically pyridine, to provide the corresponding triflate of Formula III. The triflates of Formula III are novel and provide a further embodiment of the present invention.

The triflates of Formula III are useful for the preparation of compounds of the present invention where X is —C(O) NHR$^3$ or C(O)OR$^2$ by subjecting the triflates to palladium catalyzed carbonylation conditions in the presence of a suitable amine or alcohol. A mixture of the triflate, palladium(II) acetate, 1,1'-bis(diphenylphosphine)ferrocene, a proton scavenger such as triethylamine or potassium carbonate, and a suitable amine or alcohol are combined in a suitable solvent, typically acetonitrile or dimethylformamide. The mixture is saturated with carbon monoxide and is then heated until the reaction is complete. The corresponding amides or esters are typically isolated by a standard extractive workup and purified by crystallization or chromatography. The skilled artisan will appreciate that the compounds of the invention where X is —C(O)OH are

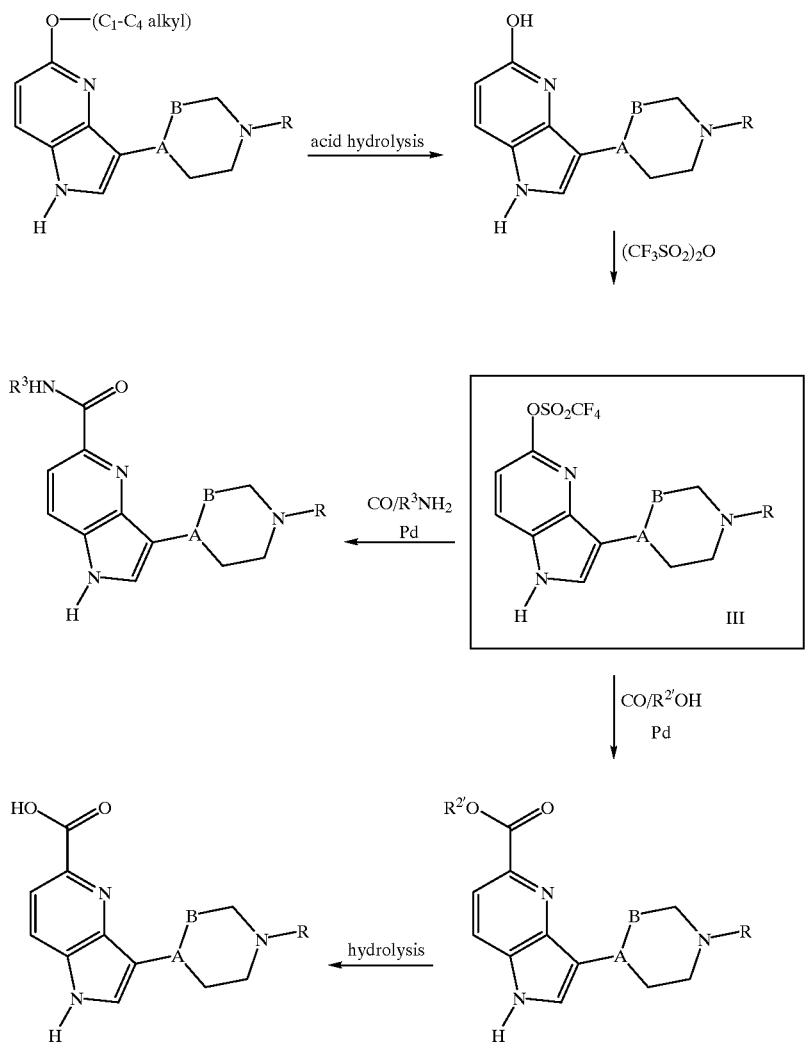

Synthetic Scheme II

An appropriate 5-alkoxypyrrolo[3,2-b]pyridine is heated with an aqueous acid, typically hydrobromic acid, to prepare the corresponding 5-hydroxypyrrolo [3,2-b]pyridine. This 5-hydroxy derivative is then treated with trifluoromethaneprepared by subjecting an appropriate ester of the present invention to acid or base hydrolysis conditions.

Compounds of the present invention where X is —C(O) OH, while valuable 5-HT$_{1F}$ agonists, are also useful intermediates for the preparation of compounds of the invention where X is —C(O)NHR³. These compounds are prepared by reacting an amine of formula R³NH₂ with an appropriate carboxylic acid or carboxylic acid derivative under standard amide bond forming conditions.

Compounds of the invention where X is —NHR¹ are prepared by functionalizing the corresponding 5-aminopyrrol-o[3,2-b]pyridine through standard acylation/reduction or reductive alkylation conditions. Briefly, a solution of the 5-aminopyrrolo[3,2-b]pyridine in a suitable solvent, such as tetrahydrofuran, dioxane, or diethyl ether, at a temperature from about ambient to about 0° C., is reacted with an appropriate acylating agent in the presence of a suitable base such as pyridine or triethylamine. This acylated product is then dissolved in a suitable solvent, such as tetrahydrofuran or diethyl ether, at a temperature from about ambient to about 0° C., and is treated with a suitable hydride reducing agent such as diborane or lithium aluminum hydride. The reaction is stirred from 1 to 24 hours and is then treated with an aqueous solution of sodium sulfate. The resultant suspension is filtered, and the filtrate concentrated under reduced pressure to provide the desired product.

Alternatively, a solution of a 5-aminopyrrolo[3,2-b]-pyridine in a solvent suitable for the azeotropic removal of water, such as toluene, benzene or cyclohexane, is reacted at reflux with an appropriate aldehyde or ketone in the presence of 0.1–10% of a proton source such as 1-toluenesulfonic acid. When the reaction is complete the volatiles are removed under reduced pressure and the residue redissolved in an alkanol such as methanol or ethanol. This solution is then subjected to hydrogenation conditions, or is treated with an appropriate hydride reducing agent, such as sodium borohydride or, preferably, sodium cyanoboro-hydride in the presence of an anhydrous acid such as hydrogen chloride. The product is isolated by a normal extractive workup.

The requisite 5-substituted pyrrolo[3,2-b]pyridines necessary for the preparation of the compounds of the present invention may be prepared as described in Synthetic Scheme III where X" is halo or C₁–C₄ alkoxy.

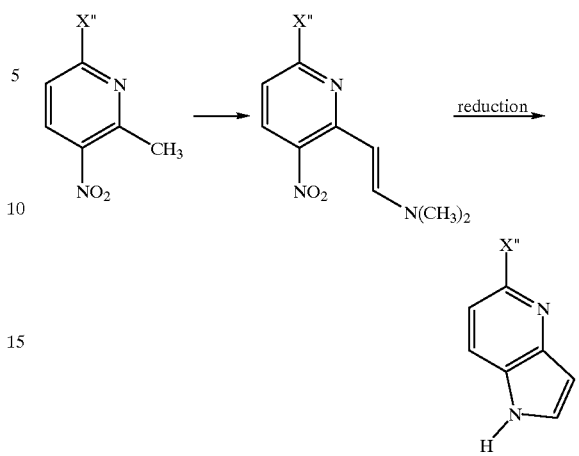

Synthetic Scheme III

The 2-methyl-3-nitro-6-substituted pyridine may be reacted with either dimethylformamide dimethylacetal in dimethylformamide or tris(dimethylamino)methane in toluene at elevated temperature to prepare the corresponding iminoenamine. Where X" is C₁–C₄ alkoxy, the iminoenamine in a lower alkanol, typically ethanol, or a mixture of the lower alkanol and tetrahydrofuran, is then hydrogenated over Raney nickel or a precious metal catalyst, typically either platinum or palladium on carbon, to provide the appropriate 5-(C₁–C₄ alkoxy)pyrrolo[3,2-b]pyridine. Where X" is halo, the iminoenamine is reacted with metallic iron in toluene/-acetic acid to provide the desired 5-halopyrrolo[3,2-b]-pyridine. The 5-substituted pyrrolo[3,2-b]pyridines may be purified by recrystallization or chromatography as necessary or desired prior to use in the preparation of the compounds of the present invention.

The 6-substituted 3-nitro-2-picolines required to prepare the corresponding 5-substituted-pyrrolo[3,2-b]pyridines are either commercially available or may be prepared by methods well known to the skilled artisan.

The requisite 5-substituted-pyrrolo[3,2-b]pyridine necessary for the preparation of the compounds of the present invention where X is —NHR¹ may be prepared as described in Synthetic Scheme IV.

Synthetic Scheme IV

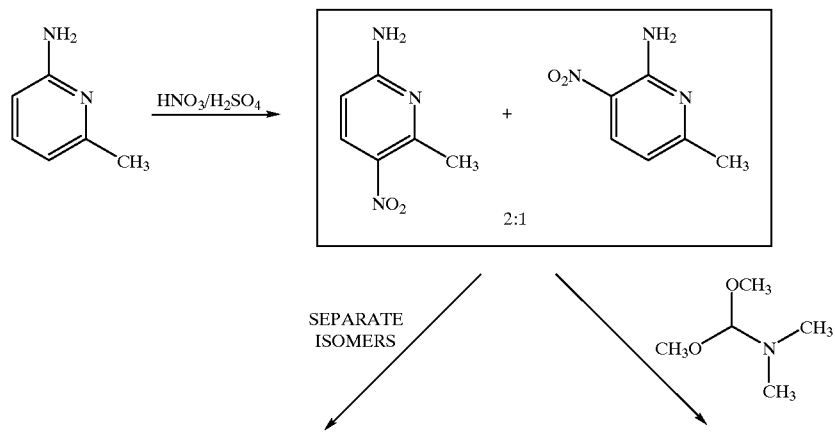

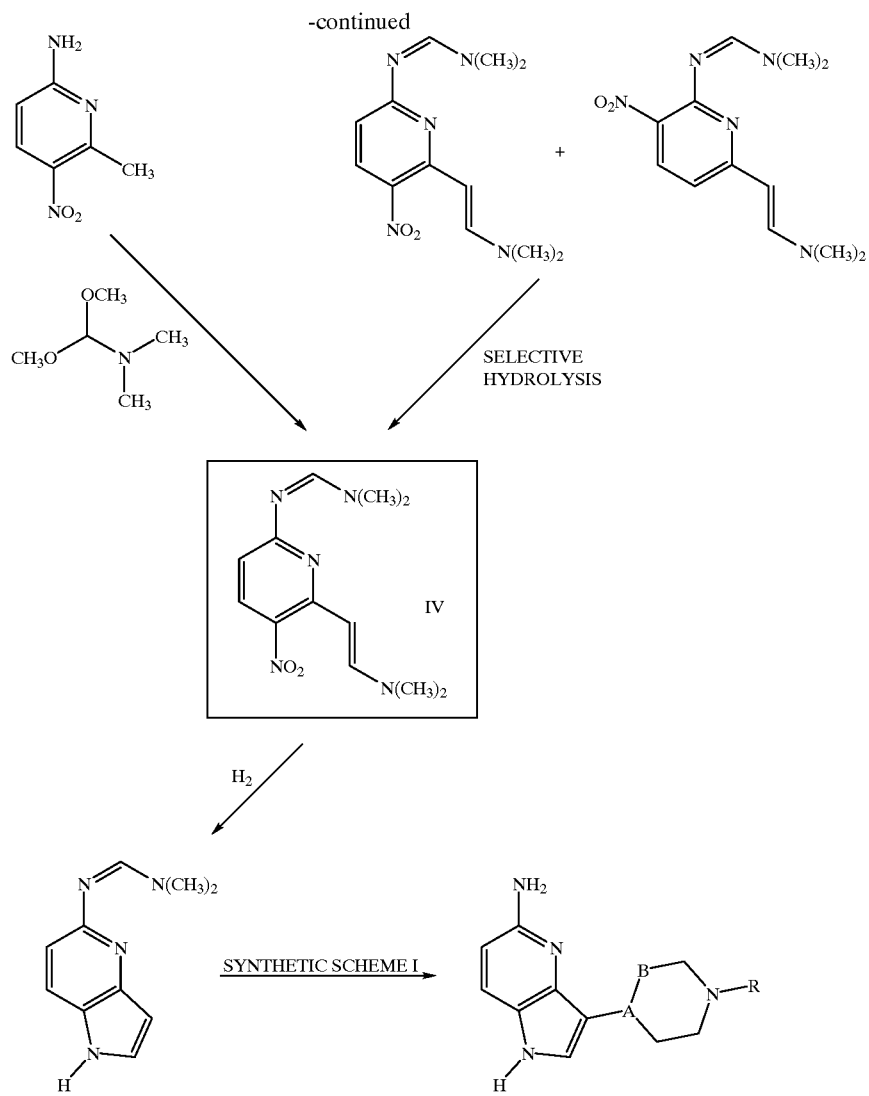

The nitration is performed by adding an equivalent of 90% nitric acid dissolved in an equal volume of concentrated sulfuric acid which has been precooled 0° C. to a solution of 6-amino-2-picoline (6-amino-2-methylpyridine) in five volumes (relative to volume of nitric acid solution) of concentrated sulfuric acid at −6° C. The nitric acid solution is added at a rate to maintain the temperature of the reaction mixture at about −2° C. The reaction mixture is stirred at about 0° C. for one hour and is then allowed to warm to about 10° C. over an hour. The temperature of the reaction mixture is maintained at about 10° C. for one hour and is then allowed to warm to about 20° C. over an hour. The reaction mixture is maintained at about 20° C. for 2 hours. The reaction mixture is then poured over ice, made basic (pH about 9) by the addition of an appropriate hydroxide base, typically potassium, sodium, or ammonium hydroxide, maintaining the temperature at about 20° C. by the addition of ice as needed. The resulting slurry is filtered, washed with water, and dried to provide a 2:1 mixture of 3-nitro-:5-nitro-6-amino-2-picoline.

The undesired 5-nitro-6-amino-2-picoline isomer may be removed by steam distillation, sublimation, or by fractional crystallization from a suitable solvent, preferably toluene. The desired 3-nitro-6-amino-2-picoline is then reacted with dimethylformamide dimethylacetal or tris(dimethylamino)-methane in a suitable solvent, typically dimethylformamide. Once the reaction is complete the reaction mixture is treated with either water or isopropanol to precipitate the desired intermediate IV, which is isolated by filtration. Alternatively, Intermediate IV may be prepared by directly subjecting the mixture of nitration isomers previously described to dimethylformamide dimethylacetal or tris(dimethylamino) methane. Treatment of the resulting reaction mixture with water results in the precipitation of Intermediate IV which may be isolated by filtration.

Intermediate IV may then be hydrogenated in a lower alkanol, typically ethanol, in the presence of a palladium catalyst, typically 10% palladium on carbon. Once hydrogenation is complete, the reaction mixture is filtered and the filtrate concentrated under reduced pressure. The desired 5-(dimethylaminomethylimino)pyrrolo[3,2-b]pyridine may be used as recovered in subsequent reactions or first purified by slurry washing or by silica gel chromatography as necessary or desired. Subjecting 5-(dimethylaminomethylimino)pyrrolo[3,2-b]pyridine to the reaction conditions described in Synthetic Scheme I provides the 5-aminopyrrolo-[3,2-b]pyridines necessary to prepare the corresponding compounds of the present invention.

Alternatively, compounds of the present invention where X is —NHR¹ may be prepared by the procedure described in Synthetic Scheme V.

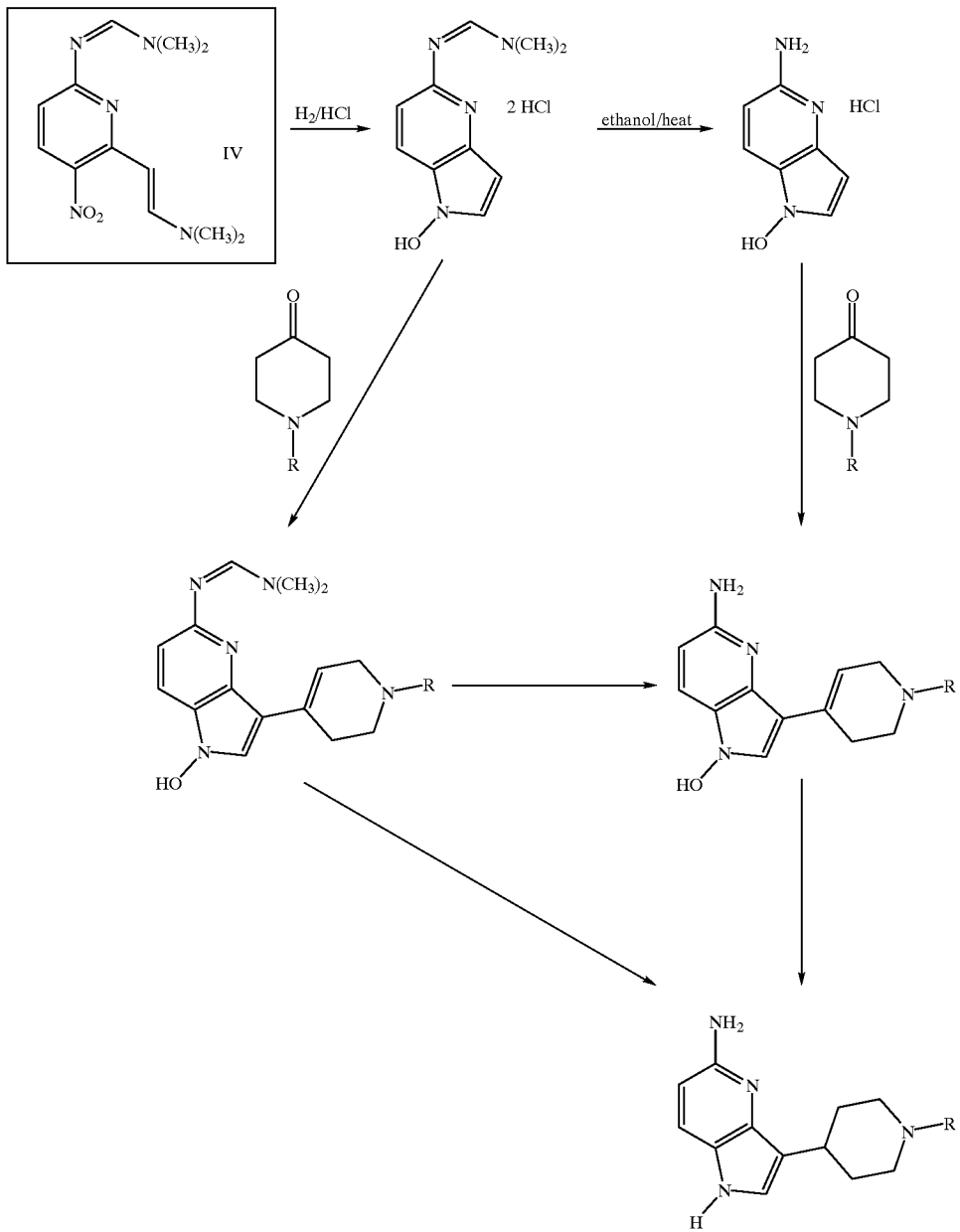

Intermediate IV is hydrogenated in methanol containing hydrogen chloride in the presence of a palladium catalyst, typically 10% palladium on carbon. The resulting 1-hydroxy-5-(dimethylaminomethaneimino)pyrrolo[3,2-b] pyridine dihydrochloride is isolated by filtration of the reaction mixture and may be further purified and removed from catalyst by recrystallization. The amidine functionality at the 5-position of the pyrrolo[3,2-b]pyridine may be removed to provide the corresponding amine by heating the amidine substrate in ethanol under acidic conditions or under neutral hydrogenation conditions. The amidine functionality at the 5-position may be removed either prior or subsequent to reaction with an appropriate 4-piperidone under the conditions described for Synthetic Scheme I to provide the requisite 5-aminopyrrolo[3,2-b]pyridines. Regardless of when the amidine functionality is removed, the 1-hydroxy substituent is removed by hydrogenation in a lower alkanol, typically methanol, in the presence of a palladium catalyst, typically 10% palladium on carbon.

The ability of the compounds of this invention to bind to the 5-HT$_{1F}$ receptor subtype was measured essentially as described in U.S. Pat. No. 5,521,196.

Membrane Preparation: Membranes were prepared from transfected Ltk- cells which were grown to 100% confluency. The cells were washed twice with phosphate-buffered saline, scraped from the culture dishes into 5 mL of ice-cold phosphate-buffered saline, and centrifuged at 200×g for 5 minutes at 4° C. The pellet was resuspended in 2.5 mL of ice-cold Tris buffer (20 mM Tris HCl, pH=7.4 at 23° C., 5 mM EDTA) and homogenized with a Wheaton tissue grinder. The lysate was subsequently centrifuged at 200×g for 5 minutes at 4° C. to pellet large fragments which were discarded. The supernatant was collected and centrifuged at 40,000×g for 20 minutes at 4° C. The pellet resulting from this centrifugation was washed once in ice-cold Tris wash buffer and resuspended in a final buffer containing 50 mM Tris HCl and 0.5 mM EDTA, pH=7.4 at 23° C. Membrane preparations were kept on ice and utilized within two hours for the radioligand binding assays. Protein concentrations were determined by the method of Bradford (Anal. Biochem., 72, 248–254 (1976)).

Radioligand Binding: [$^3$H-5-HT] binding was performed using slight modifications of the 5-HT$_{1D}$ assay conditions reported by Herrick-Davis and Titeler (J. Neurochem., 50, 1624–1631 (1988)) with the omission of masking ligands. Radioligand binding studies were achieved at 37° C. in a total volume of 250 μL of buffer (50 mM Tris, 10 mM MgCl$_2$, 0.2 mM EDTA, 10 μM pargyline, 0.1% ascorbate, pH=7.4 at 37° C.) in 96 well microtiter plates. Saturation studies were conducted using [$^3$H]5-HT at 12 different concentrations ranging from 0.5 nM to 100 nM. Displacement studies were performed using 4.5–5.5 nM [$^3$H]5-HT. The binding profile of drugs in competition experiments was accomplished using 6–12 concentrations of compound. Incubation times were 30 minutes for both saturation and displacement studies based upon initial investigations which determined equilibrium binding conditions. Nonspecific binding was defined in the presence of 10 μM 5-HT. Binding was initiated by the addition of 50 μL membrane homogenates (10–20 μg). The reaction was terminated by rapid filtration through presoaked (0.5% polyethyleneimine) filters using 48R Cell Brandel Harvester (Gaithersburg, Md.). Subsequently, filters were washed for 5 seconds with ice cold buffer (50 mM Tris HCl, pH=7.4 at 4° C.), dried and placed into vials containing 2.5 mL Readi-Safe (Beckman, Fullerton, Calif.) and radioactivity was measured using a Beckman LS 5000TA liquid scintillation counter. The efficiency of counting of [$^3$H]5-HT averaged between 45–50%. Binding data was analyzed by computer-assisted nonlinear regression analysis (Accufit and Accucomp, Lunden Software, Chagrin Falls, Ohio). IC$_{50}$ values were converted to K$_i$ values using the Cheng-Prusoff equation (Biochem. Pharmacol., 22, 3099–3108 (1973). All experiments were performed in triplicate.

Representative compounds of this invention were found to have affinity for the 5-HT$_{1F}$ receptor as measured by the procedure described supra.

As was reported by R. L. Weinshank, et al., WO93/14201, the 5-HT$_{1F}$ receptor is functionally coupled to a G-protein as measured by the ability of serotonin and serotonergic drugs to inhibit forskolin stimulated cAMP production in NIH3T3 cells transfected with the 5-HT$_{1F}$ receptor. Agonist activation of G-protein-coupled receptors also results in the release of GDP from the α-subunit of the G protein and the subsequent binding of GTP. The binding of the stable analog [$^{35}$S]GTPγS is an indicator of this receptor activation.

Membrane Preparation

Mouse LM(tk-)cells stably transfected with the human 5-HT$_{1F}$ receptor and grown in suspension were harvested by centrifugation, resuspended in 50 mM Tris-HCl, pH 7.4, in aliquots of 2×10$^8$ cells and frozen at −70° C. until the day of the assay. On the assay day, an aliquot of cells was thawed, resuspended in 35 mL of 50 mM Tris-HCl, pH 7.4, and centrifuged at 39,800×g for 10 minutes at 4° C. The resulting pellet was resuspended in 50 mM Tris-HCl, pH 7.4, incubated for 10 minutes at 37° C. and centrifuged at 39,800×g for 10 minutes at 4° C. The pellet was resuspended and centrifuged once more, with the final pellet being resuspended in 4 mM MgCl$_2$, 160 mM NaCl, 0.267 mM EGTA, 67 mM Tris-HCl, pH 7.4, such that a 200 μL aliquot contained contained approximately 15–25 μg protein.

[$^{35}$S]GTPγS Binding

All incubations were performed intriplicate in a total volume of 800 μL. Drug dilution in water, 200 μL, spanning 6 log units, was added to 400 μL of Tris-HCl, pH 7.4, containing 3 mM MgCl$_2$, 120 nM NaCl, 0.2 mM EGTA, 10 μM GDP, and 0.1 nM [$^{35}$S]GTPγS. Membrane homogenate, 200 μL, was added and then the tubes were incubated for 30 minutes at 37° C. Using a Brandel cell harvester (model MB-48R, Brandel, Gaithersburg, Md.), the incubations were then terminated by vacuum filtration through Whatman GF/B filters which had been wet with water or 20 mM Na$_4$P$_2$O$_7$ and precooled with 4 mL of ice-cold 50 mM Tris-HCl, pH 7.4. The filters were then washed rapidly with 4 mL of ice-cold 50 mM Tris-HCl, pH 7.4. The amount of radioactivity captured on the filters was determined by liquid scintillation spectrometry using an LS6000IC (Beckman Instruments, Fullerton, Calif.). GTPγS, 10 μM, defined nonspecific binding. Protein was determined by the method of Bradford (Anal. Biochem., 72, 248–254 (1976)).

Statistical Analysis

Efficacy values for test compounds were expressed as the percent binding relative to 10 μM 5-HT. Nonlinear regression analysis was performed on the concentration response curves using a four parameter logistic equation described by De Lean et al., (Mol. Pharamacol., 21, 5–16 (1982)). Analysis of variance, followed by the Tukey-Kramer Honestly Significant Difference test (JMP; SAS Institute Inc., Cary, N.C.) was performed on the pEC$_{50}$ values and the E$_{max}$ values.

Representative compounds of the present invention were tested in the [$^{35}$S]GTPγS assay and were found to be agonists of the 5-HT$_{1F}$ receptor.

The discovery that the pain associated with migraine and associated disorders is inhibited by activation of the 5-HT$_{1F}$ receptor by administration of 5-HT$_{1F}$ agonists required the analysis of data from diverse assays of pharmacological activity. To establish that the 5-HT$_{1F}$ receptor subtype is responsible for mediating neurogenic meningeal extravasation which leads to the pain of migraine, the binding affinity of a panel of compounds to serotonin receptors was measured first, using standard procedures. For example, the ability of a compound to bind to the 5-HT$_{1F}$ receptor subtype was performed as described supra. For comparison purposes, the binding affinities of compounds to the 5-HT$_{1D}$, 5-HT$_{1B}$, and 5-HT$_{1E}$ receptors were also determined as described supra, except that different cloned receptors were employed in place of the 5-HT$_{1F}$ receptor clone employed therein. The 5-HT$_{1D}$ and 5-HT$_{1B}$ receptors have recently been renamed, they were formerly named the 5-HT$_{1D\alpha}$ and 5-HT$_{1D\beta}$ receptors, respectively. (Hartig, et al., Trends in Pharmaceutical Science, 17, 103–105 (1996)). The same panel was then tested in the cAMP assay to determine their agonist or antagonist character. Finally, the ability of these compounds to inhibit neuronal protein extravasation, a functional assay for migraine pain, was measured.

The panel of compounds used in this study represents distinct structural classes of compounds which were shown to exhibit a wide range of affinities for the serotonin receptors assayed. Additionally, the panel compounds were shown to have a wide efficacy range in the neuronal protein extravasation assay as well. The panel of compounds selected for this study are described below.

Compound I

3-[2-(dimethylamino)ethyl]-N-methyl-1H-indole-5-methanesulfonamide butane-1,4-dioate (1:1) (Sumatriptan succinate)

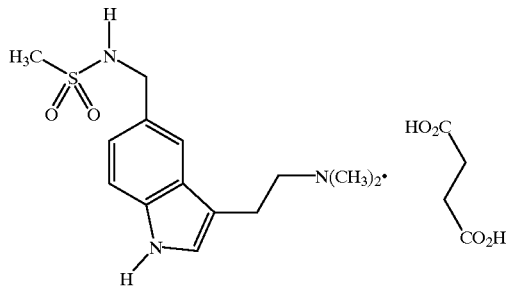

Sumatriptan succinate is commercially available as Imitrex™ or may be prepared as described in U.S. Pat. No. 5,037,845, issued Aug. 6, 1991, which is herein incorporated by reference in its entirety.

Compound II 5-fluoro-3-(1-(2-(1-methyl-1H-pyrazol-4-yl)ethyl)-4-piperidinyl)-1H-indole hydrochloride

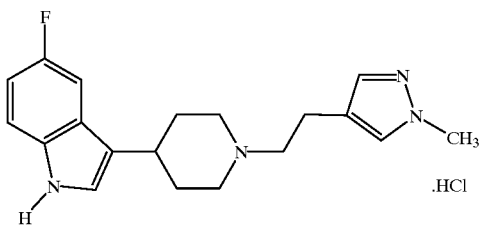

Compound III 5-hydroxy-3-(4-piperidinyl)-1H-indole oxalate

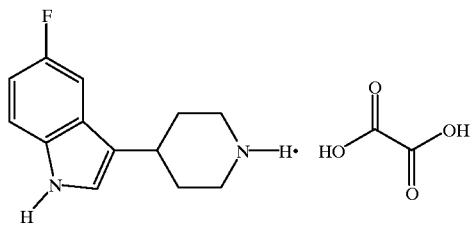

Compound IV 8-chloro-2-diethylamino-1,2,3,4-tetrahydronaphthalene hydrochloride

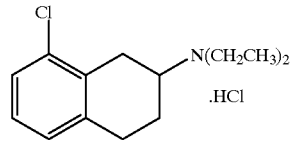

Compound V 6-hydroxy-3-dimethylamino-1,2,3,4-tetrahydrocarbazole

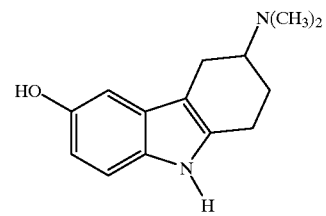

The preparation of Compounds II–V are described in U.S. Pat. No. 5,521,196, issued May 28, 1996, which is herein incorporated by reference in its entirety.

Binding Assays

The binding affinities of compounds for various serotonin receptors were determined essentially as described above except that different cloned receptors are employed in place of the 5-$HT_{1F}$ receptor clone employed therein. The results of these binding experiments are summarized in Table I.

TABLE I

| BINDING TO SEROTONIN (5-$HT_1$) RECEPTOR SUBTYPES ($K_i$ nM) | | | | |
|---|---|---|---|---|
| Compound | 5-$HT_{1D}$ | 5-$HT_{1B}$ | 5-$HT_{1E}$ | 5-$HT_{1F}$ |
| I | 4.8 | 9.6 | 2520.0 | 25.7 |
| II | 21.7 | 53.6 | 50.3 | 2.5 |
| III | 163.2 | 196.5 | 3.9 | 22.0 |
| IV | 13.5 | 145.3 | 813.0 | 129.2 |
| V | 791.0 | 1683.0 | 73.6 | 10.3 | cAMP Formation

As was reported by R. L. Weinshank, et al., WO93/14201, the 5-$HT_{1F}$ receptor is functionally coupled to a G-protein as measured by the ability of serotonin and serotonergic drugs to inhibit forskolin stimulated cAMP production in NIH3T3 cells transfected with the 5-$HT_{1F}$ receptor. Adenylate cyclase activity was determined using standard techniques. A maximal effect is achieved by serotonin. An Emax is determined by dividing the inhibition of a test compound by the maximal effect and determining a percent inhibition. (N. Adham, et al., supra,; R. L. Weinshank, et al., *Proceedings of the National Academy of Sciences (USA)*, 89,3630–3634 (1992)), and the references cited therein.

Measurement of cAMP Formation

Transfected NIH3T3 cells (estimated Bmax from one point competition studies=488 fmol/mg of protein) were incubated in DMEM, 5 mM theophylline, 10 mM HEPES (4-[2-hydroxyethyl]-1-piperazineethanesulfonic acid) and 10 μM pargyline for 20 minutes at 37° C., 5% $CO_2$. Drug dose-effect curves were then conducted by adding 6 different final concentrations of drug, followed immediately by the addition of forskolin (10 μM). Subsequently, the cells were incubated for an additional 10 minutes at 37° C., 5% $CO_2$. The medium was aspirated and the reaction was stopped by the addition of 100 mM HCl. To demonstrate competitive antagonism, a dose-response curve for 5-HT was measured in parallel, using a fixed dose of methiothepin (0.32 μM). The plates were stored at 4° C. for 15 minutes and then centrifuged for 5 minutes at 500×g to pellet cellular debris, and the supernatant was aliquoted and stored at −20° C. before assessment of cAMP formation by radioimmunoassay (cAMP radioimmunoassay kit; Advanced Magnetics, Cambridge, Mass.). Radioactivity was quantified using a Packard COBRA Auto Gamma counter, equipped with data reduction software.

All of the compounds of the panel were tested in the cAMP formation assay described supra and all were found to be agonists of the $5-HT_{1F}$ receptor.

Protein Extravasation

Harlan Sprague-Dawley rats (225–325 g) or guinea pigs from Charles River Laboratories (225–325 g) were anesthetized with sodium pentobarbital intraperitoneally (65 mg/kg or 45 mg/kg respectively) and placed in a stereotaxic frame (David Kopf Instruments) with the incisor bar set at −3.5 mm for rats or −4.0 mm for guinea pigs. Following a midline sagital scalp incision, two pairs of bilateral holes were drilled through the skull (6 mm posteriorly, 2.0 and 4.0 mm laterally in rats; 4 mm posteriorly and 3.2 and 5.2 mm laterally in guinea pigs, all coordinates referenced to bregma). Pairs of stainless steel stimulating electrodes (Rhodes Medical Systems, Inc.) were lowered through the holes in both hemispheres to a depth of 9 mm (rats) or 10.5 mm (guinea pigs) from dura.

The femoral vein was exposed and a dose of the test compound was injected intravenously (1 mL/kg). Approximately 7 minutes later, a 50 mg/kg dose of Evans Blue, a fluorescent dye, was also injected intravenously. The Evans Blue complexed with proteins in the blood and functioned as a marker for protein extravasation. Exactly 10 minutes post-injection of the test compound, the left trigeminal ganglion was stimulated for 3 minutes at a current intensity of 1.0 mA (5 Hz, 4 msec duration) with a Model 273 potentiostat/galvanostat (EG&G Princeton Applied Research).

Fifteen minutes following stimulation, the animals were killed and exsanguinated with 20 mL of saline. The top of the skull was removed to facilitate the collection of the dural membranes. The membrane samples were removed from both hemispheres, rinsed with water, and spread flat on microscopic slides. Once dried, the tissues were cover-slipped with a 70% glycerol/water solution.

A fluorescence microscope (Zeiss) equipped with a grating monochromator and a spectrophotometer was used to quantify the amount of Evans Blue dye in each sample. An excitation wavelength of approximately 535 nm was utilized and the emission intensity at 600 nm was determined. The microscope was equipped with a motorized stage and also interfaced with a personal computer. This facilitated the computer-controlled movement of the stage with fluorescence measurements at 25 points (500 μm steps) on each dural sample. The mean and standard deviation of the measurements was determined by the computer.

The extravasation induced by the electrical stimulation of the trigeminal ganglion was an ipsilateral effect (i.e. occurs only on the side of the dura in which the trigeminal ganglion was stimulated). This allows the other (unstimulated) half of the dura to be used as a control. The ratio of the amount of extravasation in the dura from the stimulated side compared to the unstimulated side dura was calculated. Saline controls yielded a ratio of approximately 2.0 in rats and 1.8 in guinea pigs. In contrast, a compound which effectively prevented the extravasation in the dura from the stimulated side would have a ratio of approximately 1.0. A dose-response curve was generated and the dose that inhibited the extravasation by 50% ($ID_{50}$) was approximated. This data is presented in Table II.

TABLE II

Inhibition of Protein Extravasation ($ID_{50}$ mMol/kg)

| Compound | i.v. $ID_{50}$ (mMol/kg) |
|---|---|
| I | $2.6 \times 10^{-8}$ |
| II | $8.6 \times 10^{-10}$ |
| III | $8.9 \times 10^{-9}$ |
| IV | $1.2 \times 10^{-7}$ |
| V | $8.7 \times 10^{-9}$ |

To determine the relationship of binding at various serotonin receptors to inhibition of neuronal protein extravasation, the binding affinity of all of the compounds to each of the $5-HT_{1D}$, $5-HT_{1B}$, $5-HT_{1E}$ and $5-HT_{1F}$ receptors was plotted against their $ID_{50}$ in the protein extravasation model. A linear regression analysis was performed on each set of data and a correlation factor, $R^2$, calculated. The results of this analysis are summarized in Table III.

TABLE III

Correlation Factor ($R^2$) for Specific $5-HT_1$ Subtype Binding Affinity vs Inhibition of Protein Extravasation

| $5-HT_1$ Subtype | Correlation Factor ($R^2$) |
|---|---|
| $5-HT_{1D}$ | 0.07 |
| $5-HT_{1B}$ | 0.001 |
| $5-HT_{1E}$ | 0.31 |
| $5-HT_{1F}$ | 0.94 |

An ideally linear relationship would generate a correlation factor of 1.0, indicating a cause and effect relationship between the two variables. The experimentally determined correlation factor between inhibition of neuronal protein extravasation and $5-HT_{1F}$ binding affinity is 0.94. This nearly ideal dependence of the $ID_{50}$ in the protein extravasation model on binding affinity to the $5-HT_{1F}$ receptor clearly demonstrates that the $5-HT_{1F}$ receptor mediates the inhibition of protein extravasation resulting from stimulation of the trigeminal ganglia.

Sumatriptan exhibits low bioavailability and relatively short duration of action. Its affinity for a number of serotonin receptor subtypes gives rise to undesirable side effects, particularly vasoconstriction, which severely limits its utility in the treatment of migraine. The compounds of this invention, however, are highly bioavailable through several routes of administration including, but not limited to, oral, buccal, intravenous, subcutaneous, intranasal, intraocular, transdermal, rectal and by inhalation. They exhibit a rapid onset and long duration of action, typically requiring only a single dose per day to maintain therapeutic levels. Since compounds of this invention are potent agonists of the $5-HT_{1F}$ receptor, extremely low doses are required to maintain therapeutic levels. Additionally, due to the high selectivity of compounds of this invention for the $5-HT_{1F}$ receptor, complications due to vasoconstriction are avoided.

Compounds of this invention also inhibit protein extravasation if administered prior or subsequent to stimulation of the trigeminal ganglia, suggesting they may be administered prior to an incipient migraine attack to prevent pain, or during a migraine attack to alleviate pain.

The ability of agonists of the 5-$HT_{1F}$ receptor in general, and the compounds of the present invention specifically, to alleviate pain is demonstrated by testing in a standard model of chronic pain (Calvino, et al. *Behavioural Brain Research*, 24, 11–29 (1987); Colpaert, *Pain*, 28, 201–222 (1987)). For example, an arthritis like state can be produced in rats days after a single injection of Freund's Complete Adjuvant or a synthetic adjuvant like lipoidal amine (N,N-dioctyldecyl-N', N-bis(2-hydroxyethyl) propanediamine) in oil (Benslay and Bendele, *Agents Actions* 34(1–2), 254–6, (1991); Bendele et al., *J Pharmacol Exp Ther* 260(1), 300–5 (1992); Meacock et al., *Ann Rheum Dis* 53(10), 653–8 (1994)). Animals treated this way develop chronically swollen and painful hindpaws resulting in increased irritability, and decreased locomotion. The ideal analgesic would increase the exploratory activity of arthritic animals toward normal without increasing or decreasing this behavior in normal animals. Analgesic compounds, for example morphine and citalopram, have been demonstrated to improve exploratory behavior in these animals (Larsen and Arnt, *Acta Pharmacol Toxicol* (*Copenh*) 57(5), 345–51 (1985)).

Analgesic Assay

Male Lewis rats (Harlan-Sprague Dawley, Inc., Indianapolis, Ind.) weighing about 225 grams are housed in clear plastic cages with ad lib access to chow and water. Rats are maintained under a 12 hours on and 12 hours off light cycle.

To produce polyarthritis, half of the rats are injected subcutaneously at the dorsal base of the tail with 7.5 mg/rat of lipoidal amine in 0.1 ml of Incomplete Freund's Adjuvant. This single lipoidal amine injection results in hindpaw inflammation which becomes obvious in about ten days. The other half of the rats receive vehicle injections. Eleven days after lipoidal amine or vehicle injection, animals are treated either orally or subcutaneously with test compound or water vehicle. One hour after treatment, individual animals are placed in activity monitors (Omnitech Electronics, Columbus, Ohio) which constitute a novel environment. The activity monitors have an "open field" area of 42×42 cm and, using infrared light beams and photocells, quantify exploratory behavior. This is accomplished using a grid of photosensors placed at floor level to measure horizontal activity. A computer analyzes the data from the sensor array. Exploratory behavior is quantified during the first 5 minutes in the chamber. The measured parameter used in this study is total distance traveled during the 5 minute test period.

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, buccal, rectal, intranasal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See, e.g., REMINGTON'S PHARMACEUTICAL SCIENCES, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.001 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.0001 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Example 1

Hard gelatin capsules containing the following ingredients are prepared:

| Ingredient | Quantity (mg/capsule) |
|---|---|
| Compound of Example 7 | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
|---|---|
| Compound of Example 9 | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

Suppositories, each containing 25 mg of active ingredient are made as follows:

| Ingredient | Amount |
|---|---|
| Compound of Example 3 | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 4

An intravenous formulation may be prepared as follows:

| Ingredient | Quantity |
|---|---|
| Compound of Example 13 | 250.0 mg |
| Isotonic saline | 1000 ml |

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compound(s), and the state of the patient.

Preparation I 5-trifluoromethanesulfonyloxy-3-(1-methylpiperidin-4-yl)pyrrolo[3,2-b]pyridine A solution of 0.90 gm (3.89 mMol) 5-hydroxy-3-(1-methylpiperidin-4-yl)pyrrolo[3,2-b]pyridine in 80 mL pyridine was cooled to 0° C. To this solution were then added 1.71 mL (10.13 mMol) trifluoromethanesulfonic anhydride and the reaction mixture was allowed to warm gradually to room temperature. After four hours the reaction mixture was quenched by the addition of saturated aqueous sodium bicarbonate and was then concentrated under reduced pressure. The residue was dissolved in 3:1 chloroform:isopropanol and this solution was washed with saturated aqueous sodium chloride. The organic phase was dried over sodium sulfate and concentrated under reduced pressure. The residue was subjected to silica gel chromatography, eluting with dichloromethane containing from 0–20% methanol. Fractions containing product were combined and concentrated under reduced pressure to provide 1.12 gm (79%) of the title compound.

m.p.=171–174° C. (dec.); MS(m/e): 364(M+1); Calculated for $C_{14}H_{16}N_3O_3SF_3 \cdot 0.25 H_2O$: Theory: C, 45.73; H, 4.52; N, 11.42. Found: C, 45.63; H, 4.45; N, 11.20.

Preparation II 5-chloropyrrolo[3,2-b]pyridine
6-hydroxy-3-nitro-2-picoline

A suspension of 3.0 gm (19.6 mMol) 6-amino-3-nitro-2-picoline in 50 mL water containing 3.5 mL concentrated sulfuric acid was heated to effect solution. The resultant solution was cooled to 0° C. and a solution of 2.0 gm (29.4 mMol) sodium nitrite in 10 mL water was added with vigorous stirring at a rate to maintain the reaction mixture ≦10° C. After 4 hours the reaction mixture was filtered. The solid was washed with water and dried under reduced pressure to provide 2.4 gm (80%) of the desired compound as a pale yellow solid.

MS(m/e): 153 (M$^+$)
6-chloro-3-nitro-2-picoline

A mixture of 2.42 gm (15.7 mMol) 6-hydroxy-3-nitro-2-picoline, 1.0 gm phosphorus pentachloride, and 0.5 mL phosphorus oxychloride was heated at 110° C. for 2.5 hours. The reaction mixture was cooled to room temperature and then an additional 0.5 gm of phosphorus pentachloride and 0.5 mL phosphorus oxychloride were added. Heating was resumed for one hour at which point the reaction mixture poured into 100 mL of an ice/water slurry. The resultant slurry is filtered and the solid dried under vacuum to provide 2.3 gm (85%) of the desired compound as a brown solid.
2-(2-dimethylaminoethen-1-yl)-3-nitro-6-chloropyridine A solution of 5 gm (29 mMol) 6-chloro-3-nitro-2-picoline in 40 mL dimethylformamide was treated with 5.83 mL (44 mMol) dimethylformamide dimethylacetal and the resulting mixture heated at 100° C. for 1.5 hours. At this point, 2 drops of triethylamine followed by 1.9 mL dimethylformamide dimethylacetal were added and heating continued for 2 more hours. The reaction mixture was concentrated under reduced pressure to provide the desired compound.
Reduction/Ring Closure A mixture of 3.07 gm (13.5 mMol) 2-(2-dimethylamino-ethen-1-yl)-3-nitro-6-chloropyridine, 6.5 gm (0.116 mole) iron and 16.4 gm silica gel in 170 mL 5:3 toluene:acetic acid was heated at 110° C. for 1 hour. The reaction mixture was filtered through a pad of celite. The filtrate was washed sequentially with aqueous sodium bisulfite, saturated aqueous sodium bicarbonate until the aqueous wash remains basic, and saturated aqueous sodium chloride. The remaining organics were dried over sodium sulfate and concentrated under reduced pressure. The residual solid was subjected to silica gel chromatography, eluting with dichloromethane containing from 0–5% methanol. Fractions containing product were combined and concentrated under reduced pressure to provide the title compound.

MS(m/e) 153 (M$^+$)

Preparation III 5-methoxypyrrolo[3,2-b]pyridine
6-methoxy-3-nitro-2-picoline 0.46 gm (20 mMol) sodium were dissolved in 15 mL anhydrous methanol. To this solution were added 2.3 gm 6-chloro-3-nitro-2-picoline in portions. The resulting mixture was stirred for 18 hours at room temperature and then 1 hour at reflux. The reaction mixture was poured into 100 mL of ice water with vigorous stirring. The suspension was filtered and the solid dried at 30° C. under reduced pressure for 18 hours to provide 2.04 gm (91%) of the desired compound as a tan solid.
2-(2-dimethylaminoethen-2-yl)-3-nitro-6-methoxypyridine A mixture of 2.0 gm (11.9 mMol) 6-methoxy-3-nitro-2-picoline and 16 mL (119 mMol) dimethylformamide dimethylacetal in 20 mL dimethylformamide was heated at 100° C. for 7 hours. The reaction mixture was concentrated under reduced pressure. The residue was treated with toluene and concentrated under reduced pressure. The residual solid was dried at 50° C. under reduced pressure for 1 hour to provide 2.70 gm (100%) of the desired compound as a red solid.
Reduction/Ring Closure A mixture of 2.5 gm (11.2 mMol) 2-(2-dimethylamino-ethen-2-yl)-3-nitro-6-methoxypyridine and 0.30 gm 10% palladium on carbon was hydrogenated at room temperature for 18 hours at an initial hydrogen pressure of 30 p.s.i. The reaction mixture was filtered and the filtrate concentrated under reduced pressure. The residue was subjected to silica gel chromatography, eluting with dichloromethane. Fractions containing product were combined and concentrated under reduced pressure to provide 1.22 gm (74%) of the title compound as a colorless solid.

Preparation IV 5-amino-3-(1-methyl-1,2,3,6-tetrahydropyridin-4-yl)pyrrolo[3,2-b]pyridine
Nitration of 6-amino-2-picoline 110 gm (1.02 mole) molten 6-amino-2-picoline were added dropwise to 500 mL concentrated sulfuric acid which had been precooled to −15° C. at rate to maintain the temperature of the sulfuric acid solution under 20° C. The solution was then cooled to about −6° C. and then a solution of 49 mL 90% nitric acid (1.16 mole) in 49 mL sulfuric acid precooled to about 0° C. was added dropwise over about 30 minutes, maintaining the temperature at about 0° C. The reaction mixture was stirred at about 0° C. for one hour and was then allowed to warm to about 10° C. over an hour. The temperature of the reaction mixture was maintained at about 10° C. for one hour and was then allowed to warm to about 20° C. over an hour. The reaction mixture was maintained at about 20° C. for 2 hours. The reaction mixture was poured into 8 L of ice with vigorous stirring. The reaction mixture was then adjusted to pH ~9 by the addition of 1.5 L concentrated ammonium hydroxide, maintaining the temperature of the reaction mixture at about 24° C. by the addition of ice as needed. The resulting slurry was filtered and the solid washed several times with water. The solid was dried at 70° C. under vacuum for 3 days to provide 135.4 gm (87%) of a 2:1 mixture of 3-nitro-:5-nitro-6-amino-2-picoline.
Separation of Nitration Isomers by Sublimation 20 gm lots of the nitration mixture were sublimed twice under vacuum at 125° C. for 6 hours each. The 5-nitro isomer was sublimed as a bright yellow powder and discarded. The 3-nitro isomer which remained in the bottom of the sublimation apparatus was collected. A total of 121 gm were sublimed to provide 60.9 gm (75.5%) of the crude 3-nitro isomer. 58 gm of the crude 3-nitro isomer were slurried in 200 mL hot 95:5 ethanol:water. The mixture was cooled to room temperature and diluted with 200 mL of water. After two hours the precipitate was collected by filtration and rinsed several times with water. The solid was dried under vacuum at room temperature to provide 38 gm (65% based on 58 gm crude) 3-nitro-6-amino-2-picoline.

MS(m/e): 153 (M$^+$); Calculated for $C_6H_7N_3O_2$: Theory: C, 47.05; H, 4.61; N, 27.44. Found: C, 47.08; H, 4.53; N, 27.53.
Separation of Nitration Isomers by Recrystallization A mixture of 20 gm of the nitration mixture and 800 mL toluene were heated at reflux for 15 minutes. The mixture was filtered at 95° C. and the mother liquors allowed to cool to room temperature. After 4 hours the crystalline solid was collected, washed with 100 mL toluene, and dried under reduced pressure at 50° C. for 16 hours to provide 13.7 gm (68%) 3-nitro-6-amino-2-picoline.
Preparation of 2-(2-dimethylaminoethen-1-yl)-5-nitro-6-(dimethylaminomethylimino)pyrrolo[3,2-b]pyridine (Intermediate IV)

A mixture of 60 gm (0.39 mole) 3-nitro-6-amino-2-picoline in 260 mL dimethylformamide was treated with 260 mL (1.83 mole) 94% dimethylformamide dimethylacetal and the solution was heated at reflux for 48 hours. The reaction was concentrated under reduced pressure and the residual solid slurried with toluene. The toluene was evaporated under reduced pressure. This procedure was repeated 5 times. The final residue was slurried with 300 mL methyl tert-butyl ether and then filtered. This solid was washed 3 times with 300 mL methyl tert-butyl ether and the black solid was finally dried under reduced pressure to provide 90.6 gm (88%) of the desired compound.

MS(m/e): 263.1 (M+); Calculated for $C_{12}H_{17}N_5O_2$: Theory: C, 54.74; H, 6.51; N, 26.60. Found: C, 54.84; H, 6.49; N, 26.79.

Preparation of 5-(dimethylaminomethylimino)pyrrolo[3,2-b]pyridine

A mixture of 90 gm (0.34 mole) Intermediate IV and 6 gm 10% palladium on carbon in 650 mL ethanol was hydrogenated at 50 p.s.i. for 45 hours. The reaction mixture was filtered and the was concentrated under reduced pressure. The residual solid was slurried for 30 minutes with 70:30 methyl tert-butyl ether:ethyl acetate, filtered and rinsed with 3×300 mL 70:30 methyl tert-butyl ether:ethyl acetate. The solid was powdered and then slurried with 200 mL 70:30 methyl tert-butyl ether:ethyl acetate. The solid was filtered and dried under reduced pressure to provide 54.5 gm (85%) of the title compound as a yellow solid.

MS(m/e): 188.2 (M+);

Condensation with 1-methyl-4-piperidone

A solution of 19.2 gm (0.10 mole) of 5-(dimethylaminomethylimino)pyrrolo[3,2-b]pyridine in 208 mL methanol was treated with 20 gm (0.30 mole) potassium hydroxide followed by 16.3 mL (0.13 mMol) 1-methyl-4-piperidone. The reaction mixture was heated under reflux for 24 hours and was then concentrated under reduced pressure. The residual solid was treated with 250 mL 9:1 ethyl acetate-:tetrahydrofuran and 50 mL methanol. The solution was cooled to 0° C. and then 200 mL cold water were added. The phases were separated and the aqueous phase was extracted well with 9:1 ethyl acetate:tetrahydrofuran. All organic phases were combined, dried over sodium sulfate and concentrated under reduced pressure. The residual solid was slurried repeatedly with 475 mL cold water to remove black impurities. The remaining solid was dried under reduced pressure to provide 17 gm (74%) of the title compound as a yellow powder.

MS(m/e): 228.1 (M+); Calculated for $C_{13}H_{16}N_4$: Theory: C, 68.39; H, 7.06; N, 24.54. Found: C, 68.13; H, 7.06; N, 24.38.

Preparation V 5-amino-3-(1-methylpiperidin-4-yl)pyrrolo[3,2-b]pyridine

A mixture of 21 gm (89.9 mMol) 5-amino-3-(1-methyl-1,2,3,6-tetrahydropyridin-4-yl)pyrrolo[3,2-b]pyridine and 10% palladium on carbon pre-wet with 30 mL ethanol in 180 mL methanol were hydrogenated at 65 p.s.i for 3 days. The catalyst was removed by filtration and the filtrate concentrated under reduced pressure. The residual solid was slurried in 120 mL ethyl acetate, filtered, and washed 3×30 mL ethyl acetate. The remaining solid was dried under reduced pressure to provide 19 gm (92%) the title compound as a light brown solid.

MS(m/e): 230 (M+); Calculated for $C_{13}H_{18}N_4$: Theory: C, 67.80; H, 7.88; N, 24.32. Found: C, 67.21; H, 7.79; N, 24.24.

Preparation VI

Alternate Isolation of Intermediate IV

A solution of 38.8 gm (0.25 mole) 3-nitro-6-amino-2-picoline in 172 mL dimethylformamide was treated with 172 mL dimethylformamide dimethylacetal and the mixture was heated at about 97° C. for 42 hours. The reaction mixture was then cooled to room temperature and was diluted with 650 mL isopropanol. The reaction mixture was allowed to stand for 18 hours at room temperature and was then cooled to 3–5° C. with stirring for an additional 2 hours. The slurry was filtered, the solid washed 2×75 mL isopropanol, and dried under reduced pressure at 45° C. for 16 hours to provide 58.9 gm (88%) of Intermediate IV.

Preparation VII

Synthesis of Intermediate IV from Mixture of Nitration Isomers

A mixture of 133 gm (0.86 mole) of a 2:1 mixture of 3-nitro:5-nitro-6-amino-2-picoline in 500 mL dimethylformamide was treated with 500 mL (3.5 mole) 94% dimethylformamide dimethylacetal and heated at reflux for 40 hours. After cooling to room temperature, the reaction mixture was divided in half and each half was poured into 10 L of water at 0° C. with vigorous stirring. After 10 minutes, the mixture was filtered and the solid was slurried/rinsed with 3×1 L of water. The solid was dried under vacuum at 65° C. for 2.5 days to provide 183 gm (81%) of the title compound as a red solid.

Preparation VIII

Alternate Synthesis of 5-amino-3-(1-methylpiperidin-4-yl)pyrrolo[3,2-b]pyridine

Preparation of 1-hydroxy-5-(dimethylaminomethylimino) pyrrol-o[3,2-b]pyridine dihydrochloride A mixture of 23.4 gm (89 mMol) Intermediate IV and 0.7 gm 10% palladium on carbon in 234 mL anhydrous methanol were treated with 140 mL 5.9N ethanolic hydrogen chloride. The resulting mixture was hydrogenated for 1.5 hours under an initial hydrogen pressure of 30 p.s.i. The reaction mixture was diluted with 585 mL ethanol and was stirred at room temperature for 1 hour at room temperature. The precipitate was filtered and rinsed with 50 mL ethanol. The solid was taken up in 1.1 L methanol, filtered, and then concentrated under reduced pressure. The residual solid was dried under reduced pressure to provide 20.5 gm (83%) of the desired compound (containing 5% 5-(dimethylaminomethylimino)pyrrolo[3,2-b]pyridine) as a yellow solid.

Preparation of 1-hydroxy-5-(dimethylaminomethylimimo)-3-(1-methyl-1,2,3,6-tetrahydropyridin-4-yl)pyrrolo[3,2-b]pyridine A mixture of 13.5 gm (48.7 mMol) 1-hydroxy-5-(dimethyl-aminomethylimino)pyrrolo[3,2-b]pyridine and 17.5 gm (155 mMol) 1-methyl-4-piperidone in 270 mL anhydrous ethanol was stirred until homogeneous. At this point 19.4 mL (109 mMol) 5.6N dimethylamine in ethanol were added and the reaction mixture stirred at room temperature for 4 hours. The yellow precipitate was filtered, washed 2×27 mL ethanol, and dried under reduced pressure at 45° C. to provide 13.4 gm (92%) of the desired compound as a yellow solid.

Hydrogenation/Hydrogenolysis

A mixture of 0.28 gm (0.94 mMol) 1-hydroxy-5-(dimethylaminomethylimimo)-3-(1-methyl-1,2,3,6-tetrahydropyridin-4-yl)pyrrolo[3,2-b]pyridine and 0.10 gm 10% palladium on carbon in 20 mL methanol was hydrogenated for about 18 hours under an initial hydrogen pressure of 50 p.s.i. The reaction mixture was filtered and the filtrate concentrated under reduced pressure to provide 0.21 gm (96%) of the title compound.

EXAMPLE 1

5-(N-[ethyl]amino)-3-(1-methylpiperidin-4-yl)pyrrolo[3,2-b]pyridine

A mixture of 0.200 gm (0.74 mMol) 5-(N-[acetyl]amino)-3-(1-methylpiperidin-4-yl)pyrrolo[3,2-b]pyridine and 0.125 gm (3.31 mMol) lithium aluminum hydride in 40 mL tetrahydrofuran was heated at 75° C. for 18 hours. The reaction mixture was cooled to 0° C. and was then treated with sodium sulfate decahydrate. After vigorous stirring the reaction mixture was filtered through a pad of celite and the filtrate concentrated under reduced pressure. The residue was subjected to flash silica gel chromatography, eluting with dichloromethane containing from 0–20% methanol. Fractions containing product were combined and concentrated under reduced pressure to provide 0.10 gm (54%) of the title compound.

m.p.=132.5–133.9° C.; MS(m/e): 258(M$^+$)

EXAMPLE 2

5-(N-[benzyl]amino)-3-(1-methylpiperidin-4-yl)pyrrolo[3,2-b]pyridine

A mixture of 0.25 gm (1.09 mMol) 5-amino-3-(1-methylpiperidin-4-yl)pyrrolo[3,2-b]pyridine, 0.5 gm molecular sieves, and 0.22 mL (2.17 mMol) benzaldehyde in 10 mL methanol was stirred at 40° C. for 5 hours. The reaction mixture was then cooled to room temperature and then 0.124 gm (3.27 mMol) sodium borohydride were added. The reaction mixture was then stirred for 30 minutes at room temperature and then the reaction mixture quenched with 1N sodium hydroxide. The reaction mixture was concentrated under reduced pressure and then the aqueous residue was extracted well with 3:1 chloroform:isopropanol. The organic phases were combined, washed with saturated aqueous sodium chloride, dried over sodium sulfate and concentrated under reduced pressure. The residue was subjected to flash silica gel chromatography, eluting with dichloromethane containing 0–10% methanol. Fractions containing product were combined and concentrated under reduced pressure to provide the title compound.

MS(m/e): 321(M+1)

EXAMPLE 3

5-(N-[thien-2-ylmethyl]amino)-3-(1-methylpiperidin-4-yl)pyrrolo[3,2-b]pyridine Beginning with 0.25 gm (1.09 mMol) 5-amino-3-(1-methylpiperidin-4-yl)pyrrolo[3,2-b]pyridine and 0.20 mL (2.17 mMol) thiophene-2-carboxaldehyde, the title compound was prepared essentially as described in Example 2.

MS(m/e): 327(M+1)

EXAMPLE 4

5-chloro-3-(1-methyl-1,2,3,6-tetrahydropyridin-4-yl)pyrrolo[3,2-b]pyridine

To a solution of 0.66 gm (4.3 mMol) 5-chloropyrrolo-[3,2-b]pyridine in 50 mL methanol were added 1.09 gm (47.6 mMol) sodium. The reaction mixture was stirred until all of the sodium had dissolved and then 1.6 mL (13 mMol) 1-methyl-4-piperidone were added. The reaction mixture was stirred at reflux for 7.5 hours and was then cooled to 0° C. To this mixture were then added hydrochloric acid until the pH of the solution was about 8. The reaction mixture was then concentrated under reduced pressure to an oil. This oil was dissolved in 3:1 chloroform:isopropanol and the resulting solution was washed sequentially with saturated aqueous sodium bicarbonate and saturated aqueous sodium chloride. The remaining organics were dried over sodium sulfate and concentrated under reduced pressure. The residue was subjected to flash silica gel chromatography, eluting with dichloromethane containing from 0–10% methanol. Fractions containing product were concentrated under reduced pressure to provide 0.30 gm (28%) of the title compound.

m.p.=230° C. (dec.); MS(m/e): 247(M$^+$); Calculated for $C_{13}H_{14}N_3Cl$: Theory: C, 63.03; H, 5.70; N, 16.96. Found: C, 63.20; H, 5.90; N, 16.82.

EXAMPLE 5

5-methoxy-3-(1,2,3,6-tetrahydropyridin-4-yl)pyrrolo[3,2-b]pyridine

A solution of 0.20 gm (1.35 mMol) of 5-methoxypyrrolo-[3,2-b]pyridine, 0.23 mg (4.05 mMol) potassium hydroxide, and 0.31 gm (2.03 mMol) 4-piperidone hydrochloride monohydrate 5 mL methanol was heated at reflux for 18 hours. The reaction mixture was then concentrated under reduced pressure and the residue partitioned between water and 3:1 chloroform:isopropanol. The organic phase was washed with saturated aqueous sodium chloride, dried over sodium sulfate and concentrated under reduced pressure. The residue was subjected to radial chromatography chromatography (2 mm silica gel plate) eluting with dichloromethane containing 20–40% methanol and 1% ammonium hydroxide. Fractions containing product were combined and concentrated under reduced pressure to provide 0.21 gm (68%) of the title compound as a yellow sold. An analytical sample was crystallized from methanol.

MS(m/e): 229(M$^+$); Calculated for $C_{13}H_{15}N_3O$: Theory: C, 68.10; H, 6.59; N, 18.33. Found: C, 68.03; H, 6.74; N, 18.50.

EXAMPLE 6

5-methoxy-3-(1-methyl-1,2,3,6-tetrahydropyridin-4-yl)pyrrolo[3,2-b]pyridine

Beginning with 0.80 gm (5.4 mMol) of 5-methoxypyrrolo-[3,2-b]pyridine and 1.2 mL (10.1 mMol) 1-methyl-4-piperidone, 1.1 gm (84%) of the title compound were recovered as a yellow solid essentially by the procedure described in Example 5. An analytical sample was recrystallized from methanol.

m.p.=202.9° C. (sub.); MS(m/e): 243(M$^+$); Calculated for $C_{14}H_{17}N_3O$: Theory: C, 69.11; H, 7.04; N, 17.27. Found: C, 69.22; H, 7.13; N, 17.47.

EXAMPLE 7

5-methoxy-3-(1-methylpiperidin-4-yl)pyrrolo[3,2-b]pyridine

Beginning with 0.50 gm (2.1 mMol) 5-methoxy-3-(1-methyl-1,2,3,6-tetrahydropyridin-4-yl)pyrrolo[3,2-b]pyridine, 0.294 gm (57%) of the title compound was prepared essentially as described in Preparation V. An analytical sample was crystallized from aqueous ethanol.

MS(m/e): 245(M$^+$); Calculated for $C_{14}H_{19}N_3O$: Theory: C, 68.54; H, 7.81; N, 17.13. Found: C, 68.40; H, 7.52; N, 16.90.

EXAMPLE 8

5-hydroxy-3-(1-methylpiperidin-4-yl)pyrrolo[3,2-b]pyridine

A solution of 1.00 gm (4.1 mMol) 5-methoxy-3-(1-methyl-piperidin-4-yl)pyrrolo[3,2-b]pyridine in 20 mL hydrogen bromide (30% in acetic acid) was heated at reflux for 48 hours. Additional 5 mL aliquots of hydrogen bromide in acetic acid were added at about 8 and 24 hours. The reaction mixture was concentrated under reduced pressure and the residue treated with 1 mL saturated aqueous sodium bicarbonate. The resulting mixture was taken up in methanol and passed over a VARIAN BOND ELUT SCX™ (Varian, Harbor City, Calif., U.S.A.) ion exchange column which had been preactivated with 10% acetic acid in methanol. The column was washed with three volumes of methanol which were discarded, and then with methanol containing ammonia. Fractions containing product were combined and concentrated under reduced pressure to provide 0.892 gm (94%) of the title compound. An analytical sample was further subjected to flash silica gel chromatography, eluting with dichloromethane containing from 10–40% methanol. Fractions containing product were combined and concentrated under reduced pressure. The residue was crystallized from methanol.

MS(m/e): 231($M^+$); Calculated for $C_{13}H_{17}N_3O$: Theory: C, 67.51; H, 7.41; N, 18.17. Found: C, 67.24; H, 7.37; N, 18.38.

EXAMPLE 9

Methyl 3-(1-methylpiperidin-4-yl)pyrrolo[3,2-b]pyridine-5-carboxylate

A mixture of 0.225 gm (0.62 mMol) 5-trifluoromethanesulfonyloxy-3-(1-methylpiperidin-4-yl)pyrrolo[3,2-b]-pyridine, 0.035 gm (0.15 mMol) palladium(II) acetate, 0.17 gm (0.31 mMol) 1,1'-bis(diphenylphosphino)ferrocene, 0.17 mL (1.2 mMol) triethylamine and 0.75 mL (18.5 mMol) methanol in 15 mL dimethylformamide was saturated with carbon monoxide by bubbling carbon monoxide through the reaction mixture for about 5 minutes. The reaction mixture was heated at 60° C. under a carbon monoxide atmosphere maintained with a balloon for 24 hours. The reaction mixture was diluted with saturated aqueous sodium chloride and then extracted well with 3:1 chloroform:isopropanol. The organic phases were combined, dried over sodium sulfate and concentrated under reduced pressure. The residue was subjected to flash silica gel chromatography, eluting with dichloromethane containing 0–20% methanol. Fractions containing product were combined and concentrated under reduced pressure to provide 0.10 gm (59.3%) of the title compound.

m.p.=199.7–201.0° C.; MS(m/e): 273($M^+$); Calculated for $C_{15}H_9N_3O_2$: Theory: C, 65.91; H, 7.01; N, 15.37. Found: C, 65.62; H, 6.77; N, 15.07.

EXAMPLE 10

N-[ethyl]3-(1-methylpiperidin-4-yl)pyrrolo[3,2-b]pyridine-5-carboxamide

A mixture of 0.150 gm (0.41 mMol) 5-trifluoromethanesulfonyloxy-3-(1-methylpiperidin-4-yl)pyrrolo[3,2-b]pyridine, 0.023 gm (0.10 mMol) palladium(II) acetate, 0.12 gm (0.21 mMol) 1,1'-bis(diphenylphosphino)ferrocene, and 0.457 gm (3.30 mMol) potassium carbonate in 40 mL acetonitrile was saturated with carbon monoxide at 0° C. To this mixture was then added 0.202 gm (2.48 mMol) ethylamine hydrochloride and the reaction mixture was heated to 65° C. under a carbon monoxide atmosphere maintained with a balloon. After 72 hours the reaction mixture was diluted with water and then extracted once with ethyl acetate followed by 3:1 chloroform:isopropanol. The organic phases were combined, dried over sodium sulfate and concentrated under reduced pressure. The residue was subjected to flash silica gel chromatography, eluting with dichloromethane containing 0–20% methanol. Fractions containing product were combined and concentrated under reduced pressure to provide 0.10 gm (84%) of the title compound.

m.p.=117–120° C.; MS(m/e): 286($M^+$); Calculated for $C_{16}H_{22}N_4O$: Theory: C, 67.11; H, 7.74; N, 19.56. Found: C, 67.17; H, 7.61; N, 19.43.

EXAMPLE 11

N-[phenyl]3-(1-methylpiperidin-4-yl)pyrrolo[3,2-b]pyridine-5-carboxamide

Beginning with 0.125 gm (0.34 mMol) 5-trifluoromethanesulfonyloxy-3-(1-methylpiperidin-4-yl)pyrrolo[3,2-b]pyridine and 0.16 mL (1.72 mMol) aniline, 0.065 gm (56%) of the title compound were prepared essentially by the procedure described in Example 10.

MS(m/e): 334($M^+$)

EXAMPLE 12

N-[2-hydroxyphenyl]3-(1-methylpiperidin-4-yl)pyrrolo[3,2-b]pyridine-5-carboxamide Beginning with 0.125 gm (0.34 mMol) 5-trifluoromethanesulfonyloxy-3-(1-methylpiperidin-4-yl)pyrrolo[3,2-b]-pyridine and 0.19 mL (1.72 mMol) 2-hydroxyaniline, 0.093 gm (77%) of the title compound were prepared essentially by the procedure described in Example 10.

MS(m/e): 351(M+1)

EXAMPLE 13

N-[4-fluorophenyl]3-(1-methylpiperidin-4-yl)pyrrolo[3,2-b]pyridine-5-carboxamide Beginning with 0.15 gm (0.41 mMol) 5-trifluoromethanesulfonyloxy-3-(1-methylpiperidin-4-yl)pyrrolo[3,2-b]-pyridine and 0.12 mL (1.24 mMol) 4-fluoroaniline, 0.058 gm (40%) of the title compound were prepared essentially by the procedure described in Example 10.

m.p.=114–116° C.; MS(m/e): 353(M+1); Calculated for $C_{20}H_{21}N_4OF$: Theory: C, 68.16; H, 6.01; N, 15.90. Found: C, 68.40; H, 6.08; N, 16.07.

EXAMPLE 14

3-(1-methylpiperidin-4-yl)pyrrolo[3,2-b]pyridine-5-carboxylic acid dihydrochloride A solution of 0.125 gm (0.46 mMol) methyl 3-(1-methylpiperidin-4-yl)pyrrolo[3,2-b]pyridine-5-carboxylate in 30 mL 1N hydrochloric acid was heated at reflux for 18 hours. The reaction mixture was concentrated under reduced pressure to provide 0.10 gm (87%) title compound.

MS(m/e): 259(M+1)

We claim:

1. A compound of Formula I:

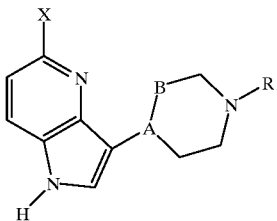

in which

A-B is —C═CH— or —CH—CH$_2$—;

R is H, C$_1$–C$_6$ alkyl, benzyl, or phenylethyl;

X is halo, hydroxy, C$_1$–C$_4$ alkoxy, —NHR$^1$, —C(O)OR$^2$, or —C(O)NHR$^3$ where:

R$^1$ is C$_1$–C$_4$ alkyl, phenyl(C$_1$–C$_4$ alkylenyl), or heteroaryl (C$_1$–C$_4$ alkylenyl);

R$^2$ is hydrogen or C$_1$–C$_4$ alkyl;

R$^3$ is C$_1$–C$_4$ alkyl, a heterocycle, or phenyl optionally monosubstituted with halo or hydroxy; and pharmaceutically acceptable acid addition salts and solvates thereof, provided that when A-B is —C═CH—, then X is not hydroxy, halogen, C$_1$–C$_4$ alkoxy, or —C(O)OR$^2$, R$^1$ is not C$_1$–C$_4$ alkyl, and R$^3$ is not C$_1$–C$_4$ alkyl.

2. A compound of claim 1 where A-B is —CH—CH$_2$—.

3. A compound of claim 1 where X is —C(O)NHR$^3$.

4. A method for the activiation of 5-HT$_{1F}$ receptors in mammals, comprising administering to a mammal in need of such activation an effective amount of a compound of Formula II:

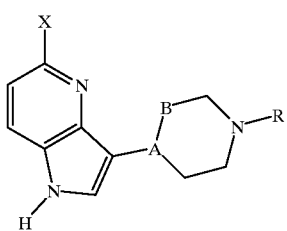

in which

A-B is —C═CH— or —CH—CH$_2$—;

R is H, C$_1$–C$_6$ alkyl, benzyl, or phenylethyl;

X is halo, hydroxy, C$_1$–C$_4$ alkoxy, —NHR$^1$, —C(O)OR$^2$, or —C(O)NHR$^3$ where:

R$^1$ is C$_1$–C$_4$ alkyl, phenyl(C$_1$–C$_4$ alkylenyl), or heteroaryl (C$_1$–C$_4$ alkylenyl);

R$^2$ is hydrogen or C$_1$–C$_4$ alkyl;

R$^3$ is C$_1$–C$_4$ alkyl, a heterocycle, or phenyl optionally monosubstituted with halo or hydroxy; and pharmaceutically acceptable acid addition salts and solvates thereof.

5. A method for the prevention of migraine in mammals, comprising administering to a mammal susceptible to migraine an effective amount of a compound of Formula II:

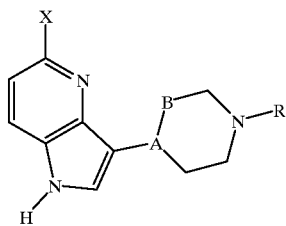

in which

A-B is —C═CH— or —CH—CH$_2$—;

R is H, C$_1$–C$_6$ alkyl, benzyl, or phenylethyl;

X is halo, hydroxy, C$_1$–C$_4$ alkoxy, —NHR$^1$, —C(O)OR$^2$, or —C(O)NHR$^3$ where:

R$^1$ is C$_1$–C$_4$ alkyl, phenyl(C$_1$–C$_4$ alkylenyl), or heteroaryl (C$_1$–C$_4$ alkylenyl);

R$^2$ is hydrogen or C$_1$–C$_4$ alkyl;

R$^3$ is C$_1$–C$_4$ alkyl, a heterocycle, or phenyl optionally monosubstituted with halo or hydroxy; and pharmaceutically acceptable acid addition salts and solvates thereof.

6. A method for the prevention or inhibition of neuronal protein extravasation, comprising administering to a mammal in need thereof an effective amount of a compound of Formula II:

in which

A-B is —C═CH— or —CH—CH$_2$—;

R is H, C$_1$–C$_6$ alkyl, benzyl, or phenylethyl;

X is halo, hydroxy, C$_1$–C$_4$ alkoxy, —NHR$^1$, —C(O)OR$^2$, or —C(O)NHR$^3$ where:

R$^1$ is C$_1$–C$_4$ alkyl, phenyl(C$_1$–C$_4$ alkylenyl), or heteroaryl (C$_1$–C$_4$ alkylenyl);

R$^2$ is hydrogen or C$_1$–C$_4$ alkyl;

R$^3$ is C$_1$–C$_4$ alkyl, a heterocycle, or phenyl optionally monosubstituted with halo or hydroxy; and pharmaceutically acceptable acid addition salts and solvates thereof.

7. A compound of the Formula III:

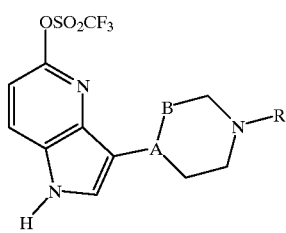

where A-B is —C═CH— or —CH—CH$_2$—; and R is H, C$_1$–C$_6$ alkyl, benzyl, or phenylethyl; and acid addition salts thereof.

8. A compound of claim 7 where A-B is —CH—CH$_2$—.

9. A compound of claim 8 where R is methyl.

10. A pharmaceutical formulation which comprises, in association with a pharmaceutically acceptable carrier, diluent, or excipient, a compound of Formula I:

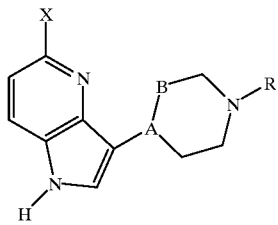

I in which

A-B is —C=CH— or —CH—$CH_2$—;

R is H, $C_1$–$C_6$ alkyl, benzyl, or phenylethyl;

X is halo, hydroxy, $C_1$–$C_4$ alkoxy, —$NHR^1$, —$C(O)OR^2$, or —$C(O)NHR^3$ where:

$R^1$ is $C_1$–$C_4$ alkyl, phenyl($C_1$–$C_4$ alkylenyl), or heteroaryl ($C_1$–$C_4$ alkylenyl);

$R^2$ is hydrogen or $C_1$–$C_4$ alkyl;

$R^3$ is $C_1$–$C_4$ alkyl, a heterocycle, or phenyl optionally monosubstituted with halo or hydroxy; and pharmaceutically acceptable acid addition salts and solvates thereof, provided that when A-B is —C=CH—, then X is not hydroxy, halogen, $C_1$–$C_4$ alkoxy, or —$C(O)OR^2$, $R^1$ is not $C_1$–$C_4$ alkyl, and $R^3$ is not $C_1$–$C_4$ alkyl.

11. A method for activation of the 5-$HT_{1F}$ receptors for the treatment of migraines in mammals, comprising administering to a mammal in need of such activation an effective amount of a compound of Formula II:

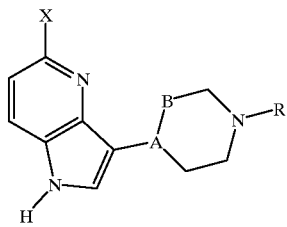

II in which

A-B is —C=CH— or —CH—$CH_2$—;

R is H, $C_1$–$C_6$ alkyl, benzyl, or phenylethyl;

X is halo, hydroxy, $C_1$–$C_4$ alkoxy, —$NHR^1$, —$C(O)OR^2$, or —$C(O)NHR^3$ where:

$R^1$ is $C_1$–$C_4$ alkyl, phenyl($C_1$–$C_4$ alkylenyl), or heteroaryl ($C_1$–$C_4$ alkylenyl);

$R^2$ is hydrogen or $C_1$–$C_4$ alkyl;

$R^3$ is $C_1$–$C_4$ alkyl, a heterocycle, or phenyl optionally monosubstituted with halo or hydroxy; and pharmaceutically acceptable acid addition salts and solvates thereof.

* * * * *